(12) United States Patent
Memita

(10) Patent No.: US 11,219,254 B2
(45) Date of Patent: Jan. 11, 2022

(54) PERSONAL PROTECTION SYSTEM AND METHOD

(71) Applicant: Pabban Development, Inc., Irvine, CA (US)

(72) Inventor: Carlo C. Memita, Laguna Hills, CA (US)

(73) Assignee: Pabban Development, Inc., Irvine, CA (US)

( * ) Notice: Subject to any disclaimer, the term of this patent is extended or adjusted under 35 U.S.C. 154(b) by 0 days.

(21) Appl. No.: 16/925,770

(22) Filed: Jul. 10, 2020

(65) Prior Publication Data

US 2021/0282476 A1    Sep. 16, 2021

Related U.S. Application Data

(60) Provisional application No. 62/989,416, filed on Mar. 13, 2020.

(51) Int. Cl.
  *A41D 13/11*    (2006.01)
  *A42B 3/22*    (2006.01)
  *A61F 9/04*    (2006.01)

(52) U.S. Cl.
  CPC ...... *A41D 13/1184* (2013.01); *A41D 13/1161* (2013.01); *A42B 3/221* (2013.01); *A61F 9/045* (2013.01); *A42B 3/225* (2013.01)

(58) Field of Classification Search
  CPC .... A41D 13/1218; A42B 3/221; A42B 3/225; A61F 9/045; A61F 11/00

(Continued)

(56) References Cited

U.S. PATENT DOCUMENTS 3,214,767 A * 11/1965 Weber .................. A61F 9/06
                                                    2/9
4,701,965 A * 10/1987 Landis ................. A61F 9/02
                                                    2/428

(Continued)

FOREIGN PATENT DOCUMENTS

| AU | 2007284105 B2 | 2/2013 |
| GB | 1404873 A | 9/1975 |
| WO | WO 2004/006815 A2 | 1/2004 |

OTHER PUBLICATIONS

3-D mask, from New York Daily News on Feb. 30, 2020 (Year: 2020).*

*Primary Examiner* — Timothy K Trieu
(74) *Attorney, Agent, or Firm* — Blair Walker IP Services, LLC

(57) ABSTRACT

A facial shield for a protective headgear system includes a polymeric sheet having an upper portion configured to be coupled to a support and a lower portion having a lower extremity, wherein the upper portion includes a first hole, a second hole, and a third hole, each one of the first, second, and third holes laterally spaced from the other two of the first, second, and third holes, and the first hole including a first section having a first hole gap and a second section laterally adjacent the first section and having a second hole gap, wherein the first hole gap of the first hole is greater than or equal to the maximum vertical dimension of a first hook of the support, and wherein the second hole gap of the first hole is greater than a vertical base thickness of a base of the first hook and is less than the maximum vertical dimension of the first hook.

27 Claims, 13 Drawing Sheets

(58) Field of Classification Search
USPC .................................................................. 2/9
See application file for complete search history.

(56) References Cited

U.S. PATENT DOCUMENTS

| | | | |
|---|---|---|---|
| 4,821,340 A | 4/1989 | Johnson | |
| 5,538,014 A | 7/1996 | Wilson et al. | |
| 5,765,223 A * | 6/1998 | McCausland | A41D 13/1184 |
| | | | 2/9 |
| 5,887,281 A | 3/1999 | Green et al. | |
| 5,970,514 A * | 10/1999 | Wang-Lee | A61F 9/045 |
| | | | 2/10 |
| 6,536,045 B1 * | 3/2003 | Wilson | A42B 3/26 |
| | | | 2/15 |
| 6,622,309 B1 * | 9/2003 | Edmonds | A63B 69/0071 |
| | | | 2/15 |
| 6,918,141 B2 | 7/2005 | Green et al. | |
| 7,752,682 B2 | 7/2010 | VanDerWoude et al. | |
| 8,234,722 B2 | 8/2012 | VanDerWoude et al. | |
| 8,336,123 B2 * | 12/2012 | Gleason | A42B 3/225 |
| | | | 2/424 |
| 8,453,262 B2 | 6/2013 | Green | |
| 10,076,627 B2 | 9/2018 | Hitchcock et al. | |
| 10,201,207 B2 | 2/2019 | VanDerWoude et al. | |
| 10,384,084 B2 | 8/2019 | Isham et al. | |
| 10,420,386 B1 | 9/2019 | Jefferis et al. | |
| 10,449,397 B2 | 10/2019 | VanDerWoude et al. | |
| 2003/0066121 A1 | 4/2003 | Diaz et al. | |
| 2007/0050898 A1 | 3/2007 | Larson et al. | |
| 2011/0265236 A1 | 11/2011 | Stoll | |
| 2012/0216341 A1 | 8/2012 | Manzella, Jr. et al. | |
| 2013/0031693 A1 | 2/2013 | Gleason et al. | |
| 2013/0327333 A1 | 12/2013 | Ng et al. | |
| 2014/0053308 A1 | 2/2014 | Cutchi | |
| 2017/0196281 A1 | 7/2017 | Rosati et al. | |
| 2019/0209912 A1 | 7/2019 | Isserow et al. | |
| 2021/0298370 A1 | 9/2021 | Watters | |
| 2021/0308499 A1 | 10/2021 | Gomes et al. | |

* cited by examiner

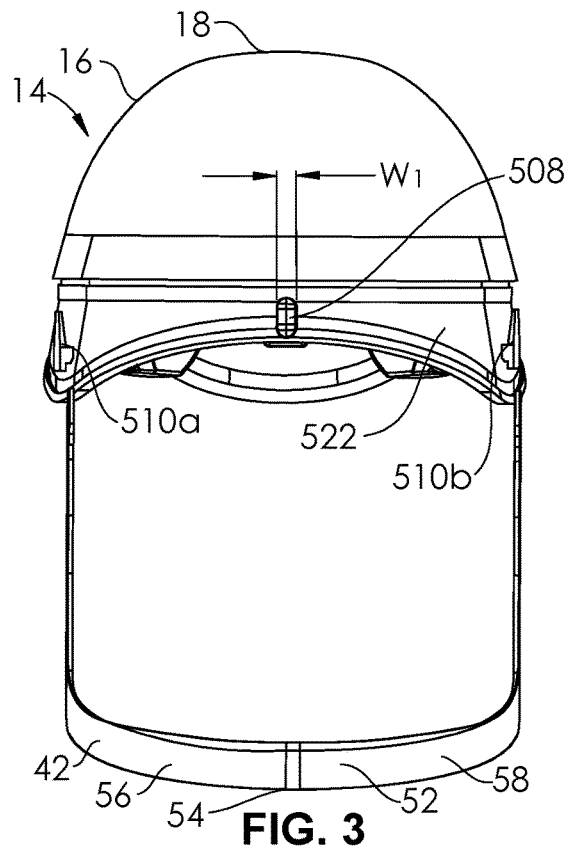
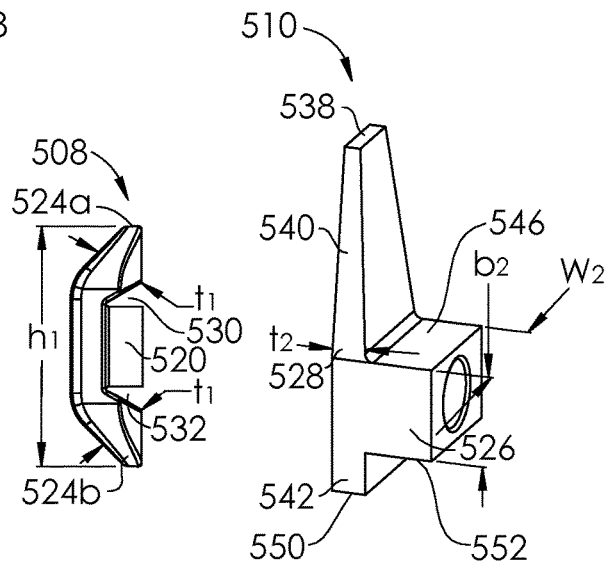
FIG. 3  FIG. 4  FIG. 5
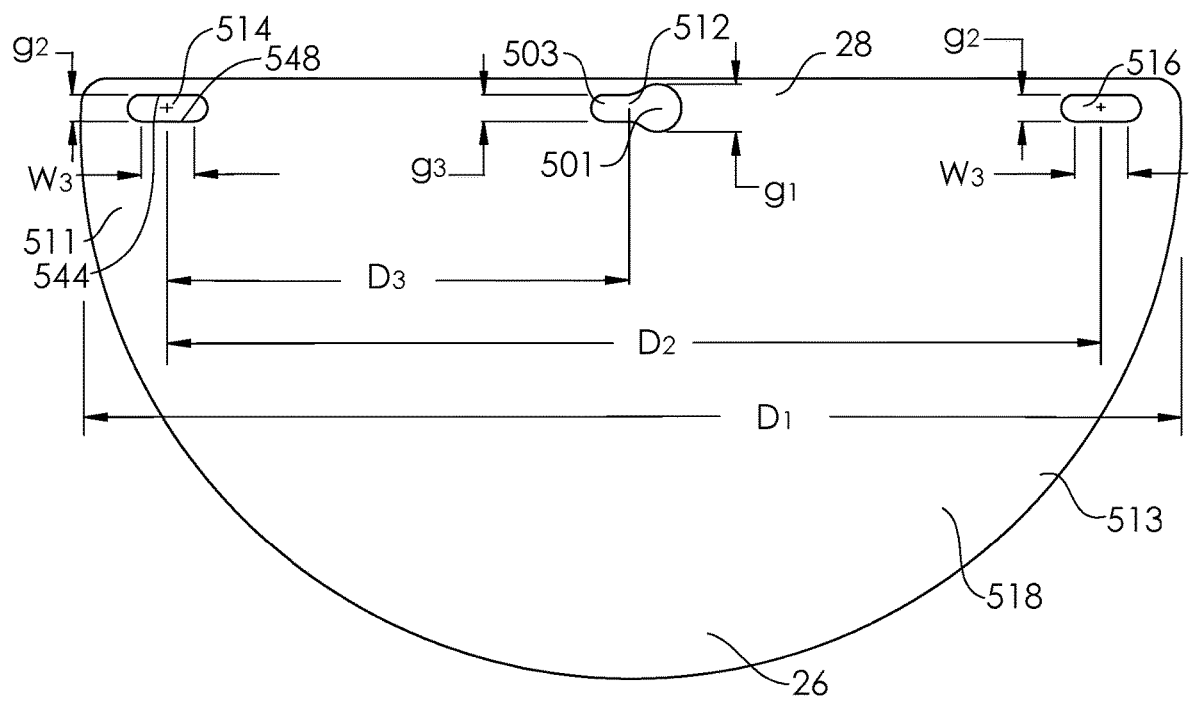
FIG. 6

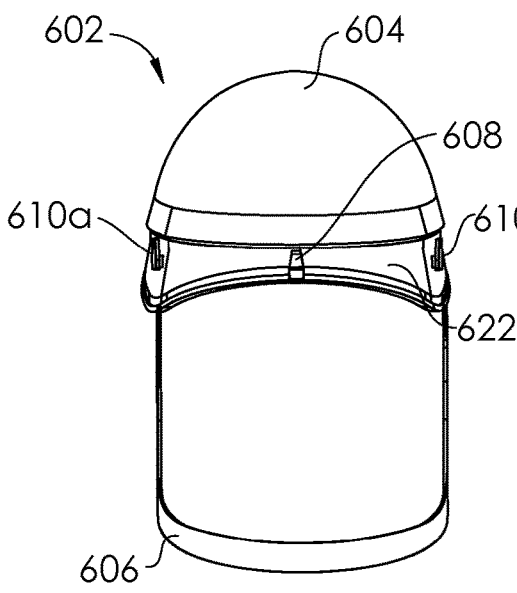
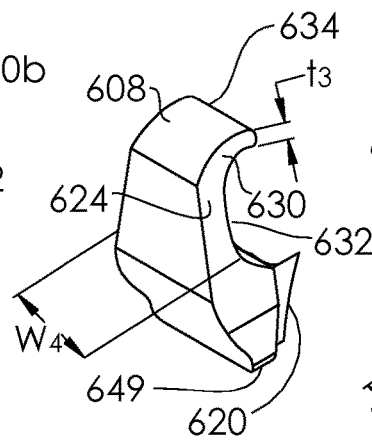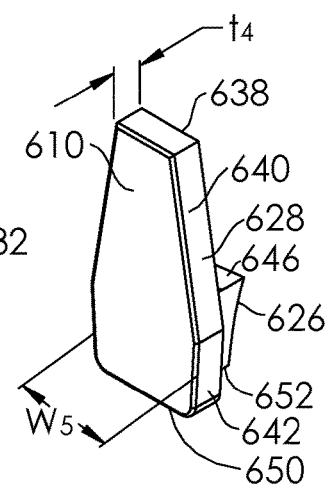
FIG. 24  FIG. 25  FIG. 26
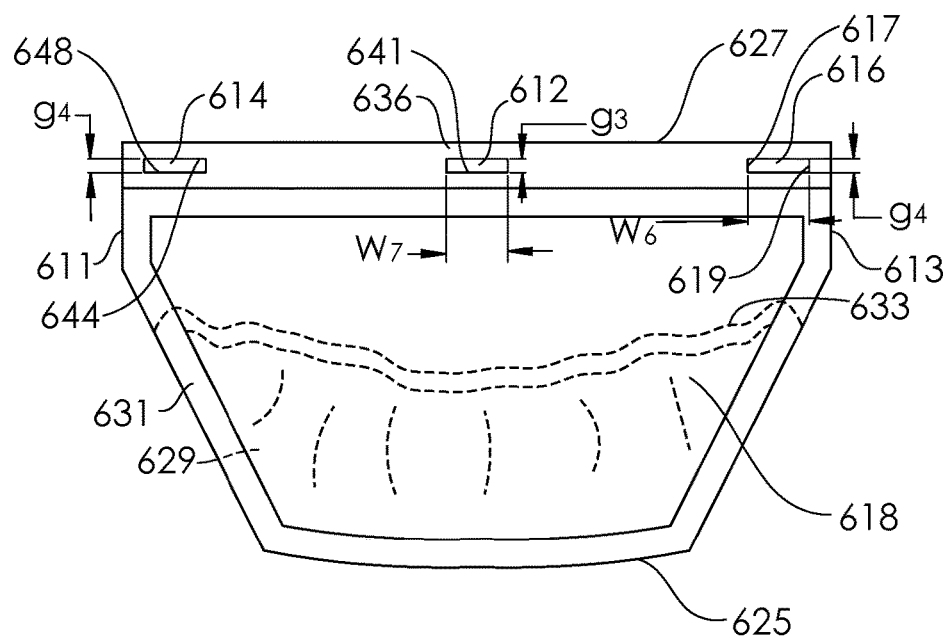
FIG. 27

PERSONAL PROTECTION SYSTEM AND METHOD

INCORPORATION BY REFERENCE TO ANY PRIORITY APPLICATIONS

This application claims the benefit of priority to U.S. Provisional Patent Application No. 62/989,416, filed on Mar. 13, 2020, which is incorporated by reference herein in its entirety for all purposes. Priority is claimed pursuant to 35 U.S.C. § 119.

BACKGROUND OF THE INVENTION

Field of the Invention

The field of the invention generally relates to personal protection systems, including, but not limited to personal environmental protections systems. The personal protections systems often include a headgear structure which is worn by an individual to protect from particulate material. The personal protection systems may provide filtered air to the user.

SUMMARY OF THE INVENTION

In one embodiment of the present disclosure, a protective headgear system includes a support configured to engage the head of a user, a facial shield including a polymeric sheet having an upper portion configured to be coupled to the support and a lower portion having a lower extremity, wherein the upper portion includes a first hole, a second hole, and a third hole, each one of the first, second, and third holes substantially spaced from the other two of the first, second, and third holes, and wherein the first and second holes are each substantially elongated, a first hook carried on the support, wherein the first hole is configured to be engaged with first hook, a second hook carried on the support, wherein the second hole is configured to be engaged with second hook, a third hook carried on the support, wherein the third hole is configured to be engaged with third hook, wherein the first hook includes a hook portion having a maximum hook width, the first hook located on a perimeter of the support between the second and third hooks, and wherein the first hole has a first hole gap and a first hole width, the first hole width of the first hole at least about 25% greater than the maximum hook width of the hook portion of the first hook.

In another embodiment of the present disclosure, a protective headgear system includes a support configured to engage the head of a user, a facial shield including a polymeric sheet having an upper portion configured to be coupled to the support and a lower portion having a lower extremity, wherein the upper portion includes a first hole, a second hole, and a third hole, each one of the first, second, and third holes laterally spaced from the other two of the first, second, and third holes, a first hook carried on the support, wherein the first hole is configured to be engaged with first hook, a second hook carried on the support, wherein the second hole is configured to be engaged with second hook, a third hook carried on the support, wherein the third hole is configured to be engaged with third hook, wherein the first hook is located on a perimeter of the support between the second hook and the third hook, wherein the first hook includes a hook portion having a maximum hook width, and wherein the first hole has a lateral width greater than the maximum hook width of the hook portion of the first hook, and wherein the facial shield has a first position in relation to the support such that the first hole can be placed over the hook portion of the first hook and the second hole is not oriented to be coupled to the second hook, and wherein the first hole is laterally slidable in relation to the first hook such that the facial shield is locked to the first hook via the first hole and such that the facial shield has a second position in relation to the support, wherein the second hole is oriented to be coupled to the second hook.

In still another embodiment of the present disclosure, a facial shield for a protective headgear system including a support configured to engage the head of a user and first, second, and third hooks carried on the support, wherein the first hook is located on a perimeter of the support between the second hook and the third hook, and wherein the first hook includes a hook portion having a maximum vertical dimension and a base coupled to the support and having a vertical base thickness, includes a polymeric sheet having an upper portion configured to be coupled to the support and a lower portion having a lower extremity, wherein the upper portion includes a first hole, a second hole, and a third hole, each one of the first, second, and third holes laterally spaced from the other two of the first, second, and third holes, and the first hole including a first section having a first hole gap and a second section laterally adjacent the first section and having a second hole gap, wherein the first hole gap of the first hole is greater than or equal to the maximum vertical dimension of the first hook, and wherein the second hole gap of the first hole is greater than the vertical base thickness of the base of the first hook and is less than the maximum vertical dimension of the first hook.

In yet another embodiment of the present disclosure, a method for donning a protective headgear system including a support configured to engage the head of a user and first, second, and third hooks carried on the support, wherein the first hook is located on a perimeter of the support between the second hook and the third hook, and wherein the first hook includes a hook portion having a maximum vertical dimension and a base coupled to the support and having a vertical base thickness, includes providing a polymeric sheet having an upper portion configured to be coupled to the support and a lower portion having a lower extremity, wherein the upper portion includes a first hole, a second hole, and a third hole, each one of the first, second, and third holes laterally spaced from the other two of the first, second, and third holes, wherein the first hole includes a first section having a first hole gap and a second section laterally adjacent the first section and having a second hole gap, wherein the first hole gap of the first hole is greater than or equal to the maximum vertical dimension of the first hook, and wherein the second hole gap of the first hole is greater than the vertical base thickness of the base of the first hook and is less than the maximum vertical dimension of the first hook, placing the first hole over the first hook, sliding the polymeric sheet in relation to the support to lock the first hole to the first hook, attaching the second hook to the second hole, and attaching the third hook to the third hole.

BRIEF DESCRIPTION OF THE DRAWINGS

FIG. 3 is a front view of the personal protection system of FIG. 1.

FIG. 4 is a side view of a center clip of the personal protection system of FIG. 3.

FIG. 5 is a perspective view of a side clip of the personal protection system of FIG. 3.

FIG. 6 is a facial shield configured to engage with the clips of the personal protection system of FIG. 3, according to an embodiment of the present disclosure.

FIG. 24 is a front view of a personal protection system according to an embodiment of the present disclosure.

FIG. 25 is a perspective view of a side clip of the personal protection system of FIG. 24.

FIG. 26 is a perspective view of a center clip of the personal protection system of FIG. 24.

FIG. 27 is a facial shield configured to engage with the clips of the personal protection system of FIG. 24, according to an embodiment of the present disclosure.

DETAILED DESCRIPTION OF THE ILLUSTRATED EMBODIMENTS

There are several types of air flow, filtration and protective systems which are known in the art. Several types of such systems are currently available on the market for use in surgical arenas, in "clean room" environments, or in hazardous/contaminated environments.

Some of the existing systems include hoods, gowns, filters, and the like. In some instances, the air filters are built into the helmet structure. Known units frequently include external sources of air such as gas cylinders, air lines or the like which are connected to the helmet structure by tubes, hoses or the like. Currently available lens/facial seal combinations, sometimes known as loose fitting hoods, are expensive to manufacture due to the geometries required for the facial seal to attach to the lens which is curved in a plane perpendicular to the seal to the face/head of the wearer. Improvements described herein related to the interface between facial shields and headgear (helmets, etc.) accommodate clean or sterile donning techniques, and improve the overall ease of donning the protective equipment and garments. In sterile procedures, any improvements that lower or minimize contact, or decomplicate the donning steps can significantly improve the likelihood of achievement and maintenance of sterility. These improvements can also minimize unnecessary contamination to other sites.

Figure 1:
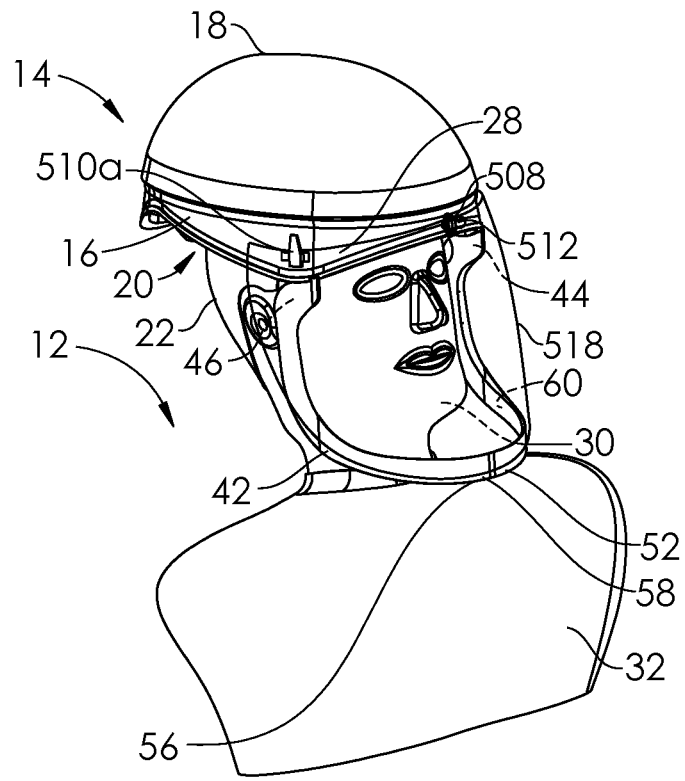
FIG. 1 is a perspective view of a personal protection system in place on a user, according to an embodiment of the present disclosure.

FIG. 1 illustrates a user 12 wearing a personal environmental protection system 14. The user 12 may be a surgeon, physician, or another medical personnel participating in a surgery or other medical procedure on a patient that has an ailment that is contagious in an otherwise standard, unprotected environment. This may also include any hospital or medical facility environment during an epidemic or pandemic that does or does not include the patient as a source of infection, such as the 2020 COVID-19 pandemic. The personal environmental protection system 14 comprises a head support 16 having a top portion 18 and a concave underside 20 configured to engage with the head 22 of the user 12. The head support 16 may comprise a helmet or other type of headgear that is securely and comfortably maintainable on the head 22 of the user 12 during an entire medical procedure, to avoid the need for constant removal, adjustment or replacement. A facial shield 518 (or lens) comprising a substantially optically clear material includes a lower extremity 26 configured to extend below the face 30 of the user 12, and an upper portion 28 configured to be coupled to the head support 16. The user 12 is able to clearly view through the facial shield 518 while the head support 16 is engaged with the head 22 of the user 12. Thus, upon movement of the head 22 of the user 12, the head support 16 maintains the facial shield 518 in front of the face 30 of the user 12. In some embodiments, a gown 32 or toga may be used by the user 12 to protect some, most, or all of the body of the user 12 below the head and neck, or at least to cover the upper torso of the user 12. In some embodiments, the gown 32 may couple directly to the facial shield 518, the head support 16, or to both the facial shield 518 and the head support 16. The personal environmental protection system 14 may be configured to substantially control the breathing environment of the use 12 via air filtration, inflow, and/or outflow, and may utilize the operative elements for air filtration, inflow, and/or outflow in any of the embodiments described in U.S. Pat. No. 8,302,599 to Green issued Nov. 6, 2012, and entitled "Protective Headgear System with Filter Protector," which is incorporated herein by reference in its entirety for all purposes. The personal environmental protection system 14 may additionally or alternatively utilize the operative elements for air filtration, inflow, and/or outflow in any of the embodiments described in U.S. Pat. No. 8,453,262 to Green issued Jun. 4, 2013, and entitled "Personal Environmental Protection Apparatus," which is incorporated herein by reference in its entirety for all purposes.

The facial shield 518 may comprise a sheet comprising high clarity polymer such as polyethylene terephthalate glycol (PETG), polyethylene terephthalate (PET), or other polyesters or polyester copolymers, or acrylic, or polycarbonate, such that it can provide a relatively thin but tough barrier that does not significantly impede the vision of the user 12. In some embodiments, the facial shield 518 may be configured to substantially control the breathing environment of the user 12 via air filtration, inflow, and/or outflow, and may utilize the operative elements for air filtration, inflow, and/or outflow in any of the embodiments has a permanent concave shape toward the user 12 and a permanent convex shape away from the user 12. In FIG. 1, however, the facial shield 518 comprises a flat flexible sheet that can be produced by die cutting or other rapid processes. The facial shield 518 is flexible and may conform to a variety of curves, such as the curve required to mate with the head support 16. In some embodiments, the facial shield 518 may comprise polycarbonate having a thickness of between about 0.010 inch and about 0.020 inch, or between about 0.012 inch and about 0.018 inch, or between about 0.014 inch and about 0.016 inch. In some embodiments, the facial shield 518 may comprise PET having a thickness of between about 0.004 inch and about 0.012 inch, or between about 0.006 inch and about 0.010 inch, or between about 0.007 inch and about 0.009 inch.

The gown 32 may comprise a number of different materials and configurations. Materials for the gown 32 may include a tri-laminate comprising a film held between two layers of non-woven plastic fabric. Bi-laminate materials are also possible, such as a material comprising a film layer and a non-woven plastic fabric. In some embodiments, the non-woven layer or layers may comprise a cellulose. In some embodiments, the non-woven layer may comprise spun materials such as spunbonded high density polyethylene (e.g., Tyvek®, a trademark of DuPont de Nemours, Inc.). In one embodiment a spunbond meltblown spunbond, commonly known as SMS, may be used, and comprises a tri-laminate non-woven fabric comprising a top layer of spunbond polypropylene, a middle layer of meltblown polypropylene and a bottom layer of spunbond polypropylene. In other embodiments, one or more of the non-woven layers may be replaced by a woven layer.

A chin bar 42 has a first end 44 connected to a first portion 48 of the head support 16 and a second end 46 connected to a second portion 50 the head support 16. The chin bar 42 may comprise a rigid polymeric material such as polyamide, for example nylon 6, or polycarbonate. The substantial rigidity allows one of the dimensions of the chin bar 42 to be relatively thin, such that it has a generally rectangular cross-section. The chin bar 42 may alternatively comprise high-density polyethylene or polypropylene, though the thin dimension would likely be thickened somewhat to maintain sufficient stiffness and resistance to extreme bending. The chin bar 42 extends between the first end 44 and the second end 46 in a generally U-shape 52 having a lower apex 54. The lower apex 54 is located at the center of a lower portion 56 of the chin bar 42 having an externally-facing surface 58 and an internally-facing surface 60.

Figure 2:
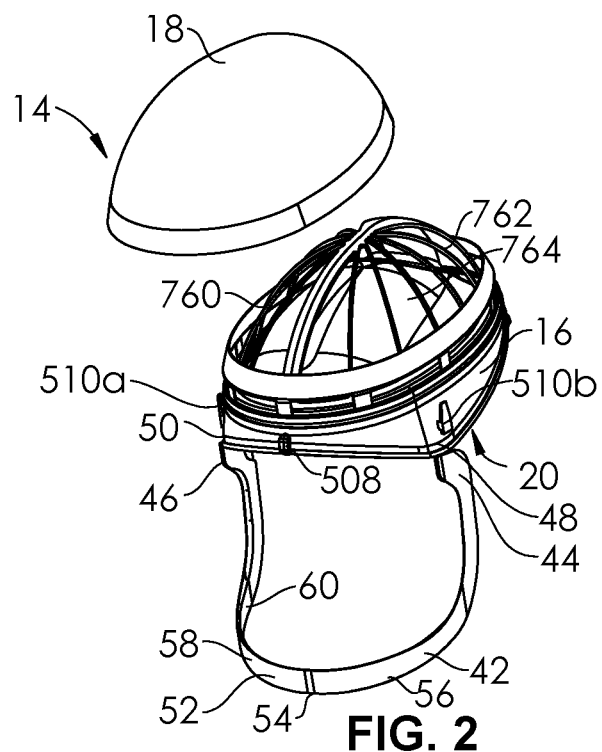
FIG. 2 is an exploded view of the personal protection system of FIG. 1.

FIG. 2 illustrates an exploded view of the personal environmental protection system 14. A filter frame 760 is carried on the head support 16 and includes a series of ribs 762 defining spaces 764 between the ribs 762 configured to allow the circulation of filtered air. A fan (not shown) is configured to cause the flow of air within the system 14. A filter cartridge/hood assembly (not shown) comprises a filter cartridge within a hood, and is configured to sealably seat on the filter frame 760.

Turning to FIG. 3, the head support 16 carries a center hook 508 and two side hooks 510a, 510b. The hooks 508, 510a, 510b are configured to engage holes 512, 514, 516 of the facial shield 518, illustrated in FIG. 6. The facial shield 518 can comprise a clear sheet of the material previously described herein. The center hook 508 (FIG. 4) has a base 520 configured to couple to an outer surface 522 of the head support 16, and a hook portion 524 comprising an upper hook portion 524a and a lower hook portion 524b, and having a height $h_1$ and a maximum width $W_1$. Each of the side hooks 510a, 510b (side hook 510, FIG. 5) has a base 526 configured to couple to the outer surface 522 of the head support 16, and a hook portion 528 having a maximum width $W_2$. Holes 514, 516 each have a width $W_3$ that is greater than the maximum width $W_2$. Holes 514, 516 each have a gap $g_2$ that is greater than the base height $b_2$.

The upper hook portion 524a and the lower hook portion 524b of the center hook 508 each have a maximum thickness $t_1$. The hook portion 528 of the side hooks 510 comprises an upper hook portion 540 and a lower hook portion 542. The upper hook portion 540 of the side hooks 510 has a maximum thickness $t_2$. Hole 512 comprises a first section 501 and a second section 503, adjacent the first section 501. Any of the holes 512, 514, 516 described herein may be formed as part of a die-cutting process, or may be added by use of a punch tool.

Figure 7:
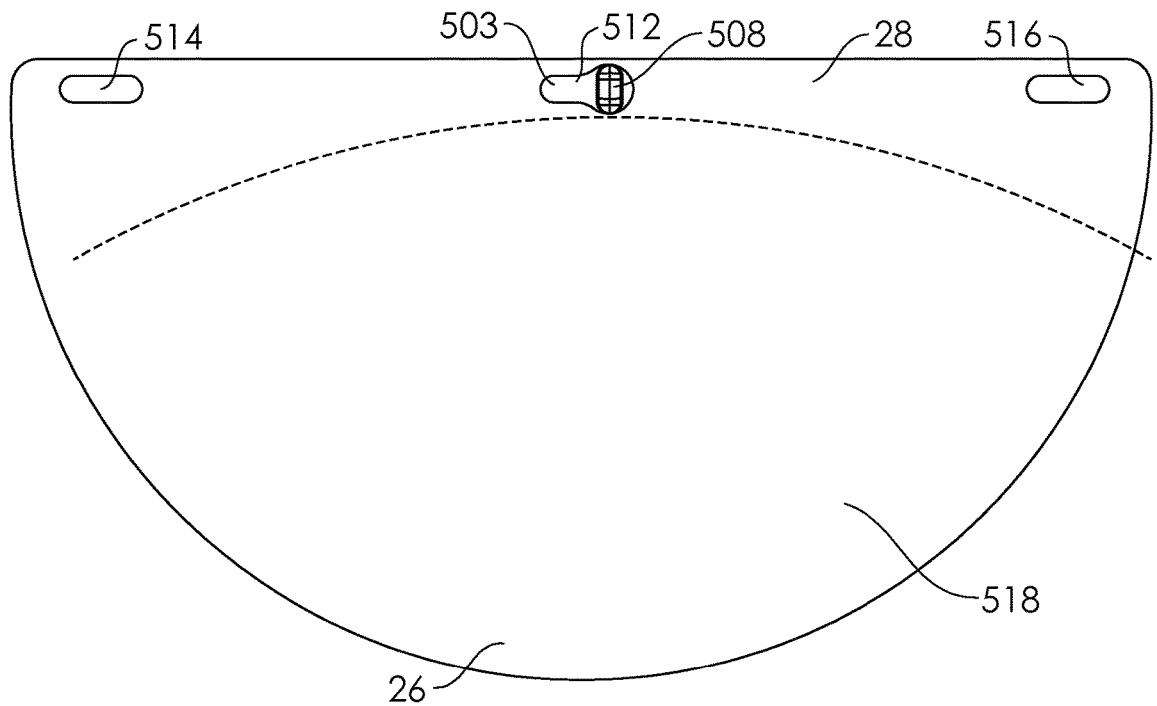
FIG. 7 is a facial shield in a first position in relation to a center clip, according to an embodiment of the present disclosure.

Turning to FIG. 7, the first section 501 of hole 512 comprises a circular shape having a maximum gap $g_1$ that is at least slightly greater than the height $h_1$ of the center hook 508. Thus, as shown in FIG. 7, the first section 501 of the hole 512 of the facial shield 518 may be placed completely over center hook 508. By then sliding the facial shield 518 in relation to the center hook 508 (arrow, FIG. 8), upper border 505 and lower border 507 are slid underneath the upper hook portion 524a and the lower hook portion 524b, respectively, thus locking the center hook 508 to the facial shield 518, via the hole 512. Holes 514, 516 each have a gap $g_2$ that is at least slightly greater than the maximum thickness $t_2$ of the upper hook portion 540 of the side hooks 510, thus allowing each hole 514, 516 to fit completely over each side hook 510a, 510b. Center hook 508 has an upper recess 530 and a lower recess 532 (FIG. 4), between the base 520 and the upper and lower hook portions 524a, 524b, respectively.

Figure 8:
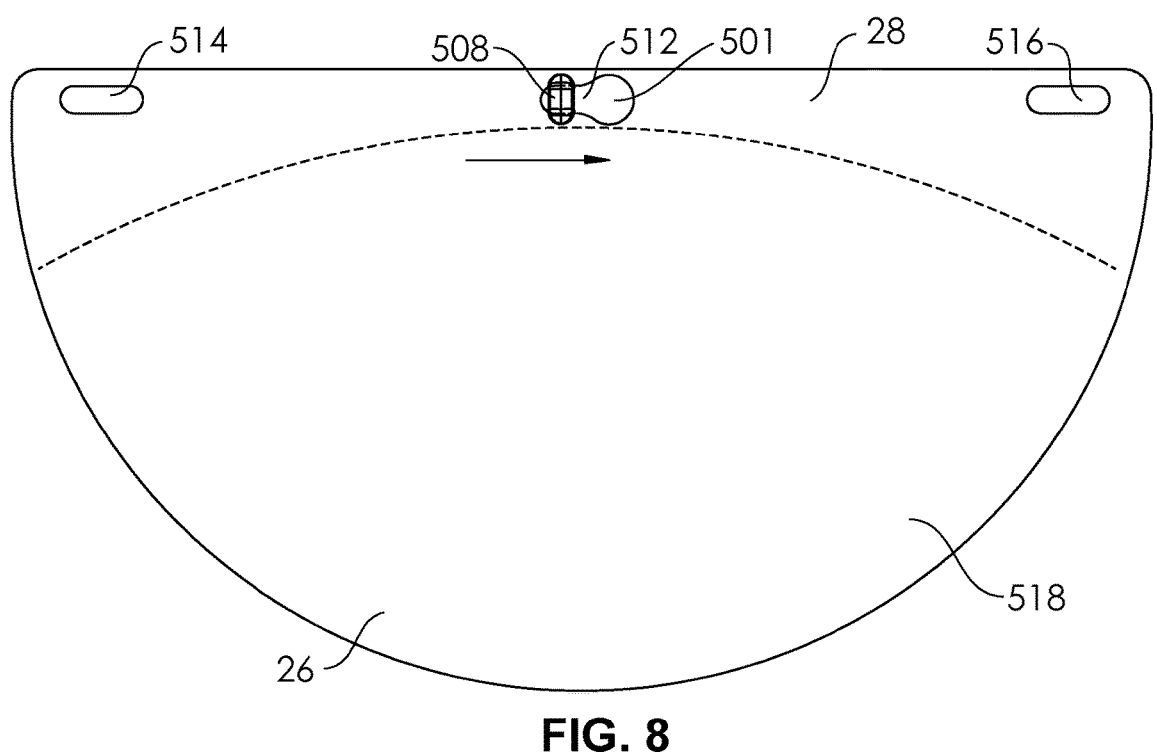
FIG. 8 is the facial shield of FIG. 7 is a second position in second, locked position in relation to the center clip.

To attach the facial shield 518 to the head support 16, the hole 512 is first inserted over the center hook 508, as in FIG. 7, and then moved in the direction of the arrow in FIG. 8, so that the hole 512 slides and locks to the center hook 508. The second section 503 of the hole 512 has a gap $g_3$ that is greater than the diameter of the base 520. In some embodiments, the base 520 may be non-circular, and thus the gap $g_3$ is greater than a vertical height of the base 520. The second section 503 of the hole 512 now straddles the base 526. As will be shown, with the first section 501 of the hole 512 around the center hook 508, as in FIG. 7, and the facial shield 518 wrapped around the outer surface 522 (perimeter) of the head support 16, the hole 514 does not align with the side hook 510a, and the hole 516 does not align with the side hook 510b. However, after the facial shield 518 has been locked in to the position of FIG. 8, with the second section 503 of the hole 512 straddling the base 526, the hole 514 aligns with the side hook 510a and the hole 516 aligns with the side hook 510b. Thus, a user 12 or a support personnel may first lock the facial shield 518 to the center hook 508, and then, with the facial shield 518 securely coupled and also balanced around the center hook 508, the user 12 or support personnel may proceed to fully attach the facial shield 518 to the side hooks 510a, 510b.

Figure 23:
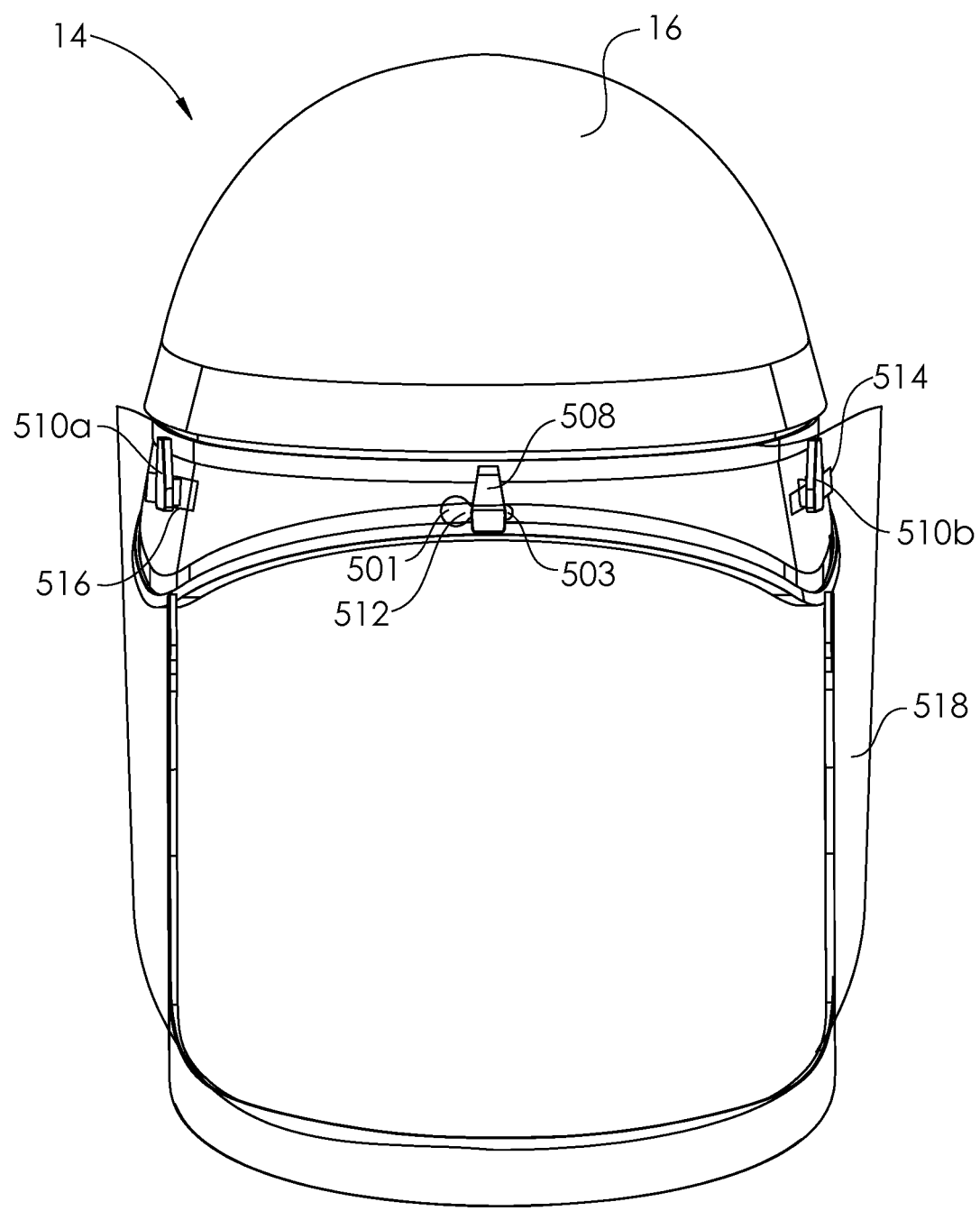
FIG. 23 is a front view of the personal protection system of FIG. 3 with the facial shield coupled to the head support.

To attach the hole 514 to the side hook 510a, the hole 514 is inserted over the end 538 (FIG. 5) of the upper hook portion 540 of the hook portion 528 of the hook 510a and the right side 511 of the facial shield 518 is pulled down over the upper hook portion 540 toward the base 526. An upper edge 544 of the hole 514 is forced against an upper ledge 546 of the base 526, and the right side 511 of the facial shield 518 is forced further downward, slightly opening the gap $g_2$, such that a lower edge 548 of the hole 514 clears a bottom face 550 of a lower hook portion 542 of the hook portion 528. When the hole 514 is released, and loses its slight deformation, the lower edge 548 of the hole 514 is snapped into its locked, rest position, above the bottom face 550, but below a lower ledge 552 of the base 526. The hole 514 is thus locked both in relation to the upper hook portion 540 and the lower hook portion 542. The facial shield 518 thus extends substantially vertically downward at its right side, as well as at its center. If needed or desired, the facial shield 518 can now be moved slightly to the left or right (e.g., by pulling on the left side 513 or the right side 511 of the facial shield 518), with the hole 514 sliding (though still in a locked position) along the side hook 510a and with the second section 503 of the hole 512 sliding (though remaining in a locked position) along the base 520 of the center hook 508. The total width of the holes 512, 514, 516 in relation to the hooks 508, 510a, 510b determines how much lateral play there is in the locked condition. The snapping process of the hole 514 and the side hook 510a can be repeated with the hole 516 and the side hook 510b on the left side 513 of the facial shield 518. Once all holes 512, 514, 516 have been coupled to the hooks 508, 510a, 510b, the facial shield 518 is now securely in place on the head support 16, with a few quick and simple snap and slide actions, as shown in FIG. 23. Furthermore, the facial shield 518 can be attached to the head support 16 without the need for the user or support personnel (whichever is assembling the equipment) to touch the head support 16 in any way. This can significantly increase the likelihood of effective sterility. Oftentimes, the head support 16 is a reusable item while the facial shield 518 is supplied sterile. Though the head support 16 may be cleanable and may even be sterilizable, the avoidance of contact can assure a higher probability of a sterile procedure. In overtaxed, overwhelmed emergency rooms or surgical suites, either during pandemics or during out-of-control war or disaster situations, simplicity in setup can be important. Otherwise, mistakes can easily be made, with loss of sterility as one possible outcome.

Figure 9:
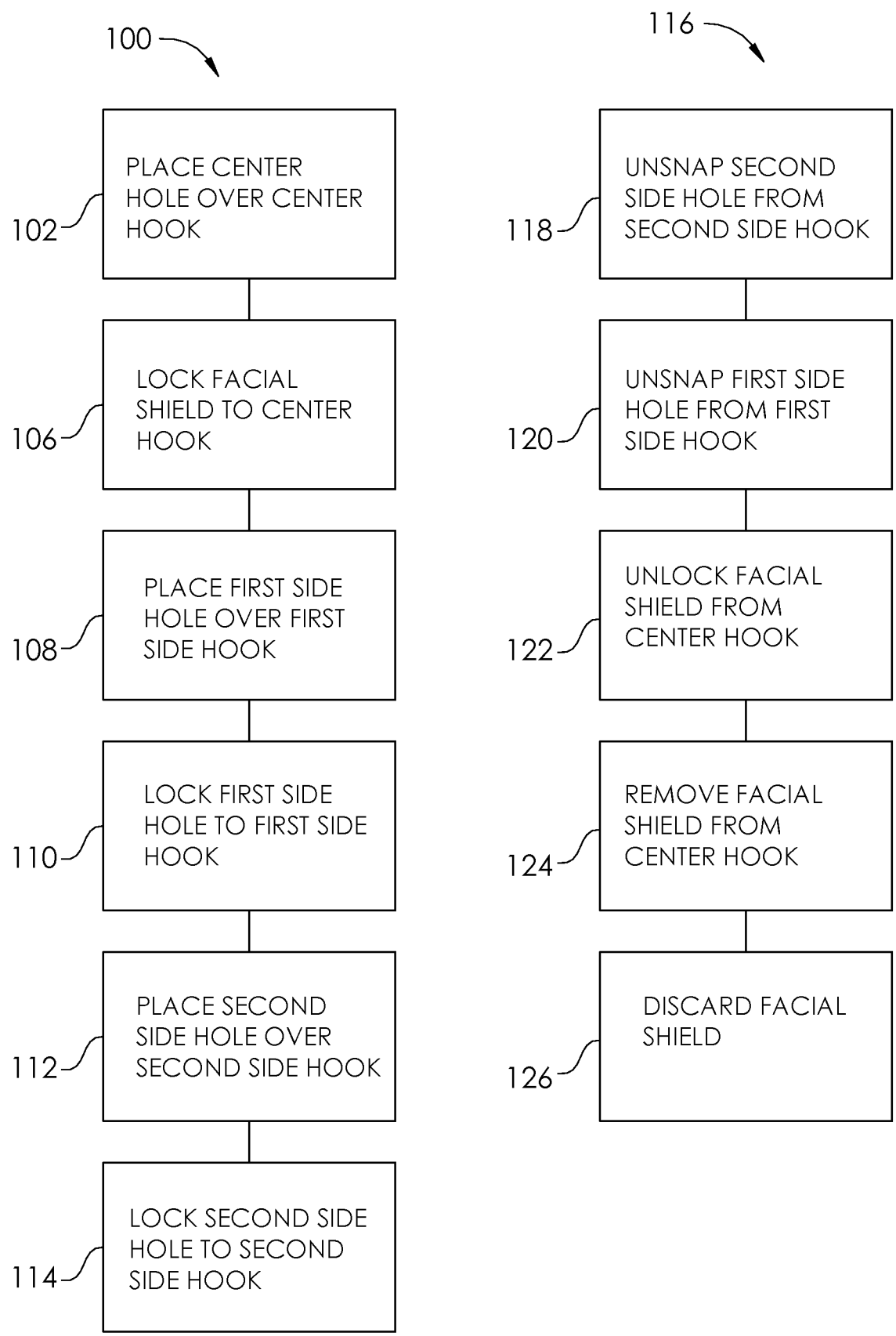
FIG. 9 is a flow chart for a method for attaching a facial shield to a head support, according to an embodiment of the present disclosure.
Figure 10:
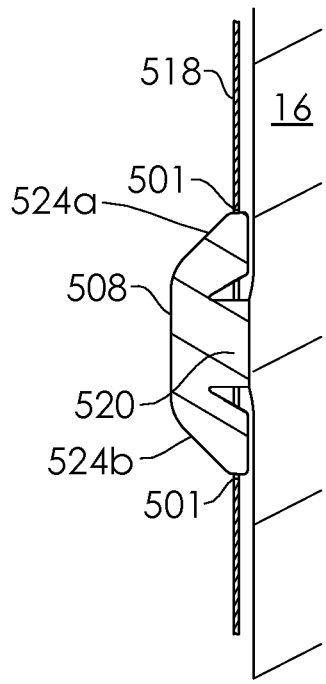
FIG. 10 is a cross-sectional view of a facial shield being assembled onto a center clip, according to an embodiment of the present disclosure.
Figure 15:
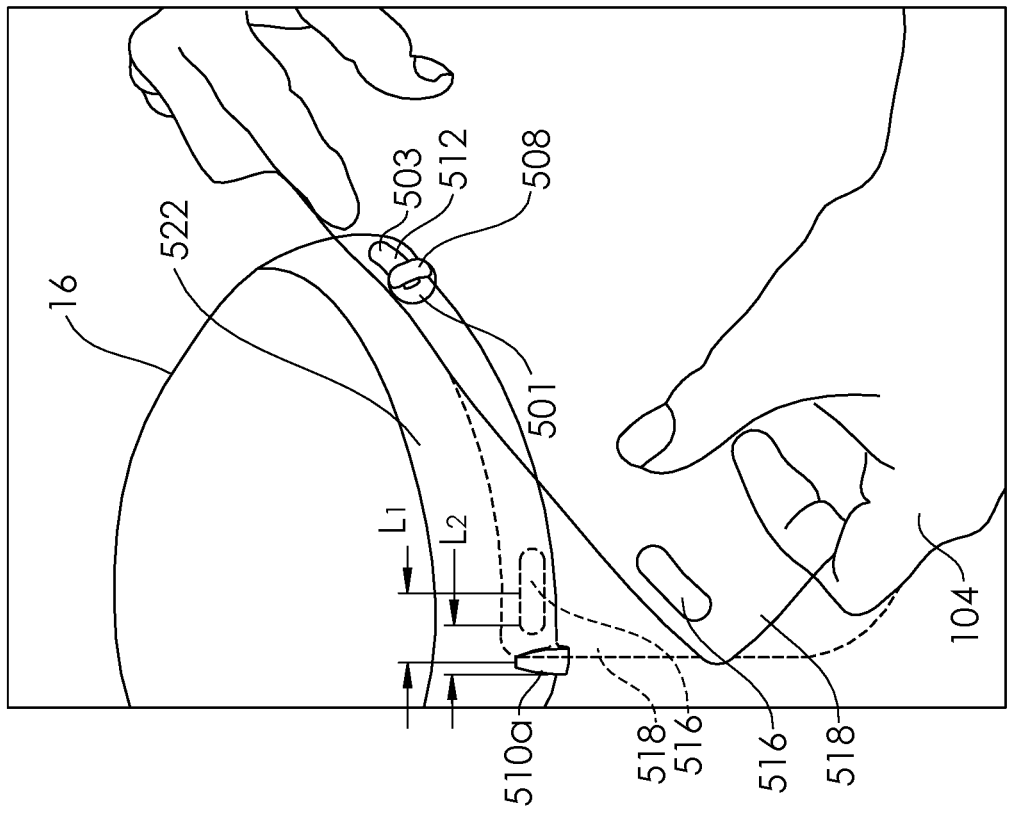
FIG. 15 is a perspective view of the facial shield being attached to the center clip, according to an embodiment of the present disclosure.
Figure 18:
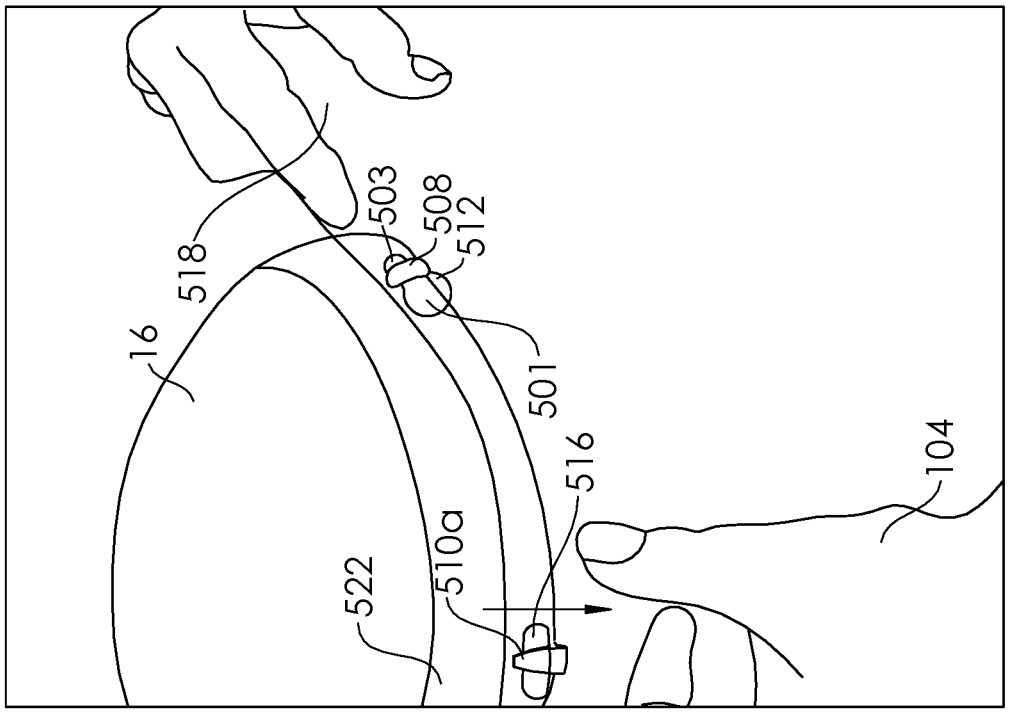
FIG. 18 is a perspective view of the facial shield being attached to the first side clip, according to an embodiment of the present disclosure.

FIG. 9 illustrates a method 100 for attaching the facial shield 518 to the head support 16. In step 102 an assembler 104 (FIG. 15), who may be a user or a support personnel, aligns the first section 501 of the hole 512 of the facial shield 518 over the center hook 508. Note that the first section 501 and the second section 503 are oriented right-to-left in FIG. 15, while they are shown left-to-right in FIG. 6. The facial shield 518 may reversible, such that it can be oriented on the head support 16 in either manner. In other embodiments, the facial shield 518 may have a non-reflective coating on only one side, and may be reversible, or non-reversible. In other embodiments, the facial shield 518 may have one or more clear peelable adhesively-attached coverings on the outer surface, which can be removed if soiled or contaminated, e.g., by splashing, or scratching. Turning to FIG. 10, the diameter (gap $g_1$) of the first section 501 of the hole 512 is shown just clearing the height $h_1$ of the center hook 508 during step 102. This position is also shown in FIG. 7. In some embodiments, the gap $g_1$ is at least slightly larger than the height $h_1$ such that the first section 501 can clear the center hook 508, as the facial shield 518 is placed over it. In some embodiments, the gap $g_1$ (FIG. 6) is the same dimension as the height $h_1$, or slightly smaller than the height $h_1$, such that the facial shield 518 can be forced over the center hook 508 without great effort from the assembler 104.

Figure 11:
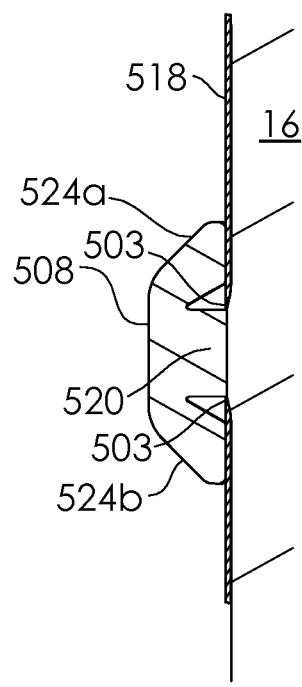
FIG. 11 is a cross-sectional view of the facial shield in assembled configuration on the center clip, according to an embodiment of the present disclosure.
Figure 16:
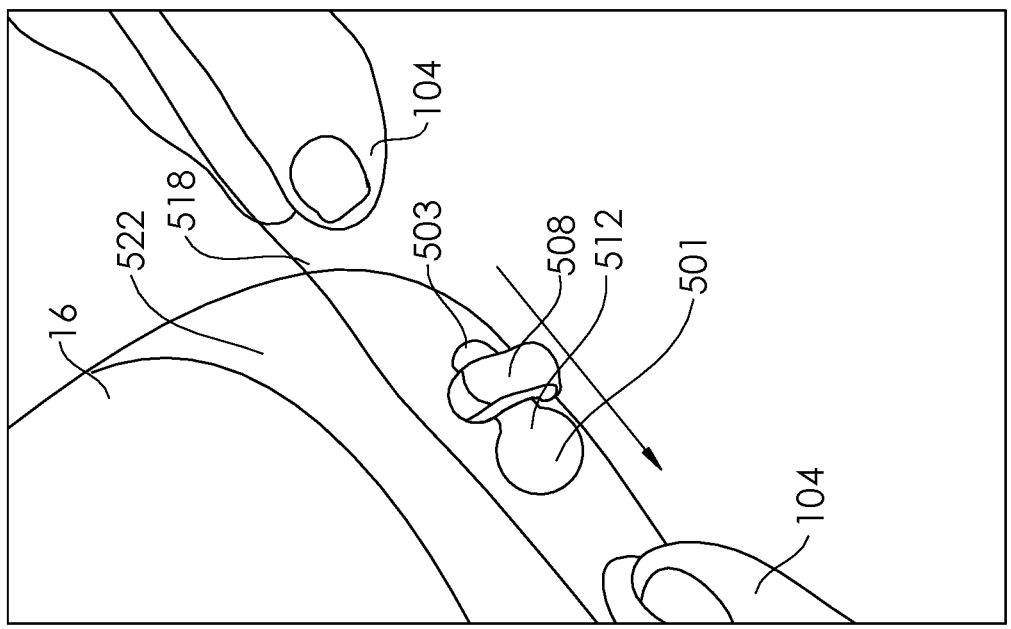
FIG. 16 is a detail perspective view of the facial shield being locked to the center clip, according to an embodiment of the present disclosure.

In step 106, the assembler 104 locks the facial shield 518 to the head support 16 by sliding the head support to the left (arrow), as shown in FIG. 16, into the position shown in FIG. 8. The second section 503 of the hole 512 is now oriented around the base 520 of the center hook 508. The center hook 508, thus, locks the facial shield 518 to the head support 16, because the gap $g_3$ (FIG. 6) is less than the height $h_1$. This can be seen in more detail in FIG. 11. Though the assembler 104 in FIGS. 15-22 is shown facing the outside of the head support 16, a user having the head support 16 upon their head may perform the same steps, for example, while looking at themself in a mirror or video monitor. In the position shown in FIG. 15 and FIG. 7, the hole 516 cannot be placed over the side hook 510a (see dashed lines in FIG. 15) when the facial shield 518 is wrapped around the outer surface 522 of the head support 16. Not only are the centers of the side hook 510a and the hole 516 (dashed) offset by a distance $L_1$, but the entirety of the hole 516 is offset from the entirety of the side hook 510a by a distance $L_2$. However, when the facial shield 518 is slid into the position shown in FIGS. 16-18, the hole 516 can be placed over the side hook 510a. Thus, it is not possible to assemble hole 516 onto the side hook 510a before assembling and locking the hole 512 onto the center hook 508. The hole 512 must be attached and locked to center hook 508 first. Thus, it is assured that during the initial locked securement of the facial shield 518 to the head support 16, the facial shield 518 is significantly centered and balanced, with no portion of it able to significantly hang too low, where it may be damaged, soiled, or contaminated. This will be further described in the following steps.

In one particular embodiment: the distance $D_1$ is between about 12.5 inches and about 18.5 inches, or between about 14 inches and about 17 inches, or between about 14.5 inches and about 16.5 inches, or about 15.5 inches; the distance $D_2$, between the horizontal center of hole 514 and the horizontal center of hole 516, is between about 11 inches and about 15 inches, or between about 12 inches and about 14 inches, or between about 12.5 inches and about 13.5 inches, or between about 12.75 inches and about 13.25 inches, or about 13 inches; the gap $g_1$ is between about 0.60 inch and about 0.75 inch, or about 0.675 inch, and is formed by a hole having a diameter of between about 0.60 inch and about 0.75 inch, or about 0.675 inch, or greater; the gap $g_2$ is between about 0.225 inch and about 0.680 inch, or between about 0.300 inch and about 0.450 inch, or between about 0.325 inch and about 0.425 inch, or about 0.375 inch; the gap $g_3$ is between about 0.325 inch and about 0.425 inch, or about 0.375 inch; the width $W_1$ is between about 0.30 inch and about 0.40 inch, or about 0.35 inch; the width $W_2$ is between about 0.35 inch and about 0.45 inch, or about 0.40 inch; the width $W_3$ is between about 0.70 inch and about 0.80 inch, or about 0.75 inch; the height $h_1$ is between about 0.61 inch and about 0.74 inch, or between about 0.65 inch and about 0.71 inch, or about 0.68 inch; the thickness $t_1$ is between about 0.10 inch and about 0.18 inch, or between about 0.12 inch and about 0.16 inch, or about 0.14 inch; the thickness $t_2$ is between about 0.06 inch and about 0.14 inch, or between about 0.08 inch and about 0.12 inch, or about 0.10 inch; the base height $b_2$ is between about 0.225 inch and about 0.325 inch, or between about 0.250 inch and about 0.300 inch, or about 0.275 inch; the distance $D_3$, between the horizontal center of hole 512, approximately where section 501 transitions to section 503, and the horizontal center of hole 514, is between about 6.0 inches and about 7.0 inches, or between about 6.25 inches and about 6.75 inches, or about 6.50 inches. In other embodiments, the gap $g_1$ is greater than or equal to 0.68 inch.

Figure 12:
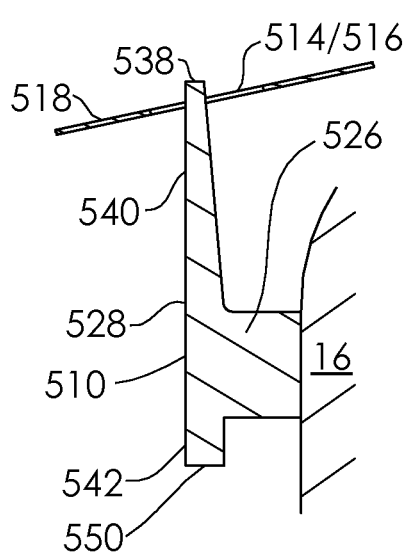
FIG. 12 is a cross-sectional view of the facial shield being assembled onto a side clip, according to an embodiment of the present disclosure.
Figure 13:
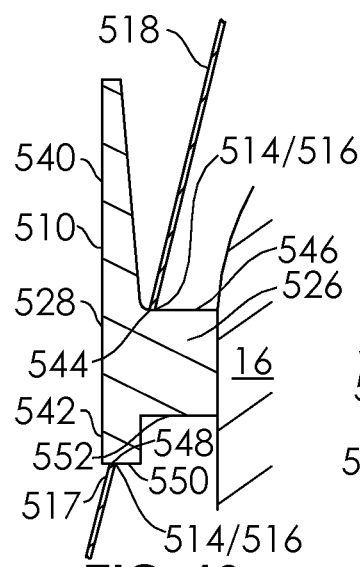
FIG. 13 is a cross-sectional view of the facial shield further being assembled onto the side clip, according to an embodiment of the present disclosure.
Figure 14:
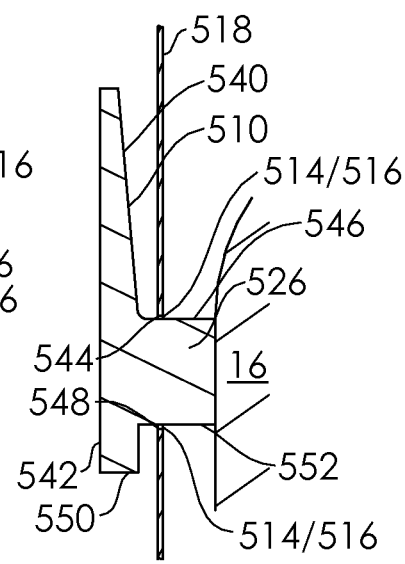
FIG. 14 is a cross-sectional view of the facial shield in assembled configuration on the side clip.
Figure 17:
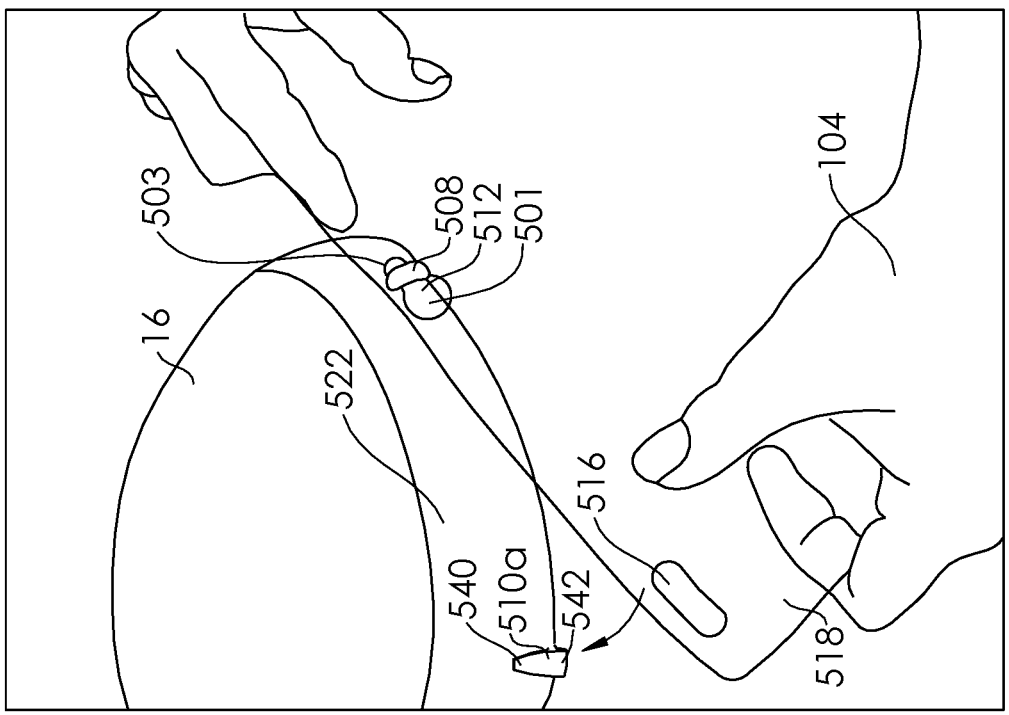
FIG. 17 is a perspective view of the facial shield being adjusted prior to assembly to a first side clip, according to an embodiment of the present disclosure.
Figure 19:
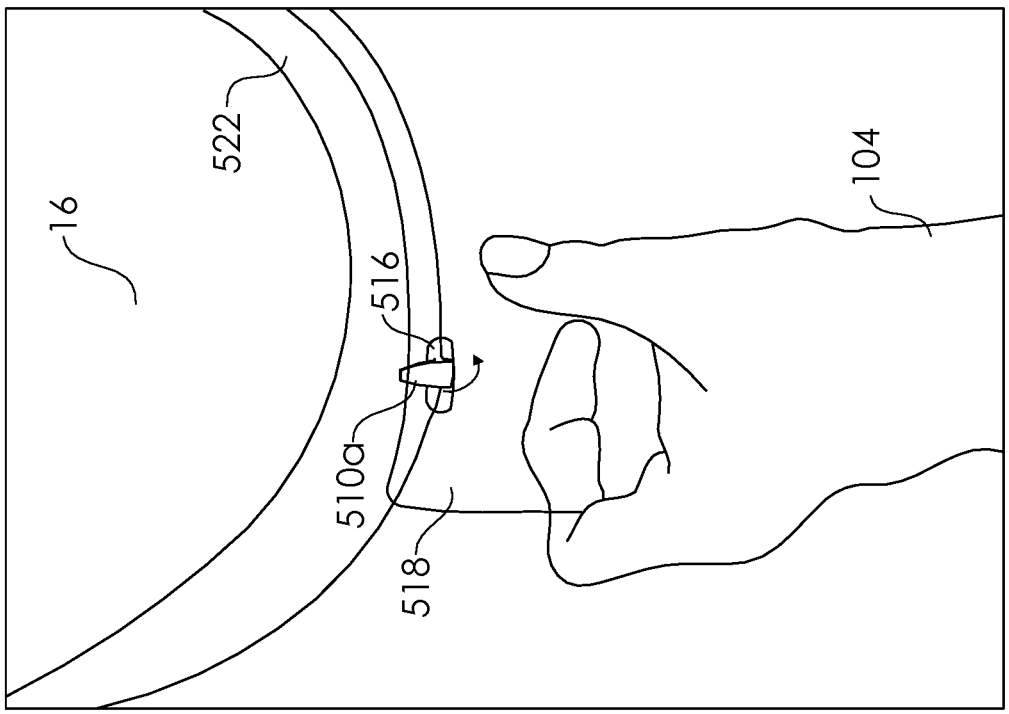
FIG. 19 is a perspective view of the facial shield being locked to the first side clip, according to an embodiment of the present disclosure.

In step 108, the assembler 104 wraps the facial shield 518 around the outer surface 522 of the head support 16 and places the hole 516 over the upper hook portion 540 of the side hook 510a, as shown in FIG. 17. As shown in detail in FIG. 12, the assembler 104 passes the hole 516 over the end 538 and onto the upper hook portion 540 of the hook portion 528 of the hook 510a. In step 110, the assembler 104 pulls the facial shield 518 downward (arrow, FIG. 18) to force a lower margin 517 of material surrounding the hole 516 over the bottom face 550 of a lower hook portion 542 of the hook portion 528, as shown in FIG. 13 and FIG. 19. An upper edge 544 of the hole 516 is forced against an upper ledge 546 of the base 526, and the right side of the facial shield 518 is forced further downward, slightly opening the gap $g_2$ (FIG. 6), such that a lower edge 548 of the hole 516 clears a bottom face 550 of a lower hook portion 542 of the hook portion 528. Turning to FIG. 14, when the hole 516 is released, and loses its slight deformation, the lower edge 548 of the hole 516 is snapped into its locked, rest position, above the bottom face 550, but below a lower ledge 552 of the base 526. The hole 516 is thus locked both in relation to the upper hook portion 540 and the lower hook portion 542.

Figure 20:
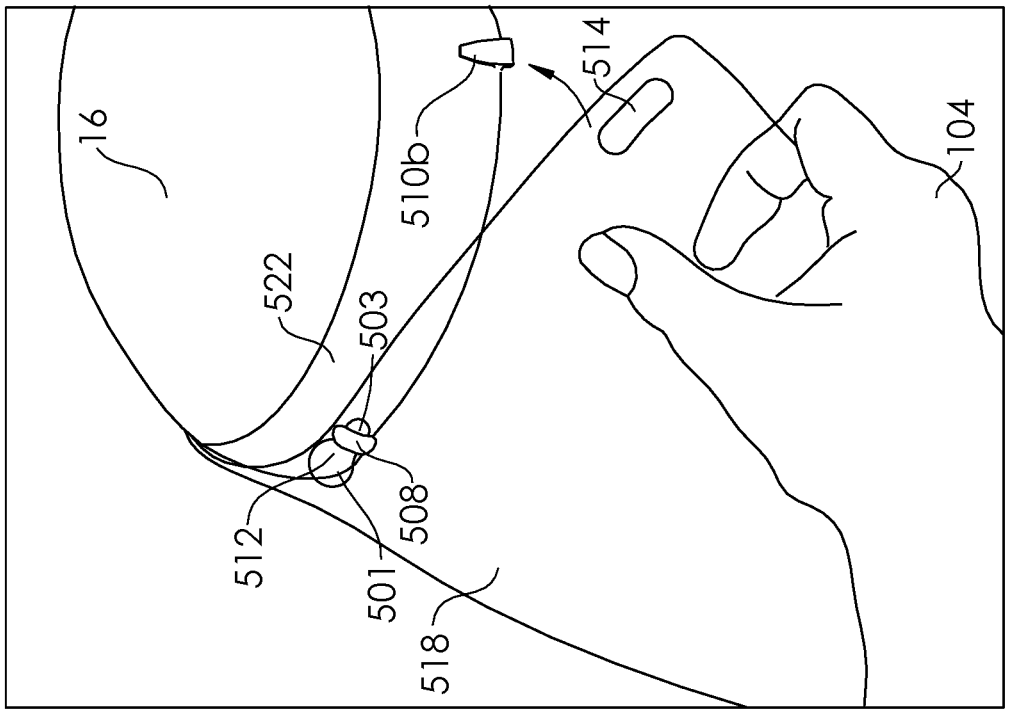
FIG. 20 is a perspective view of the facial shield being adjusted prior to assembly to a second side clip, according to an embodiment of the present disclosure.
Figure 22:
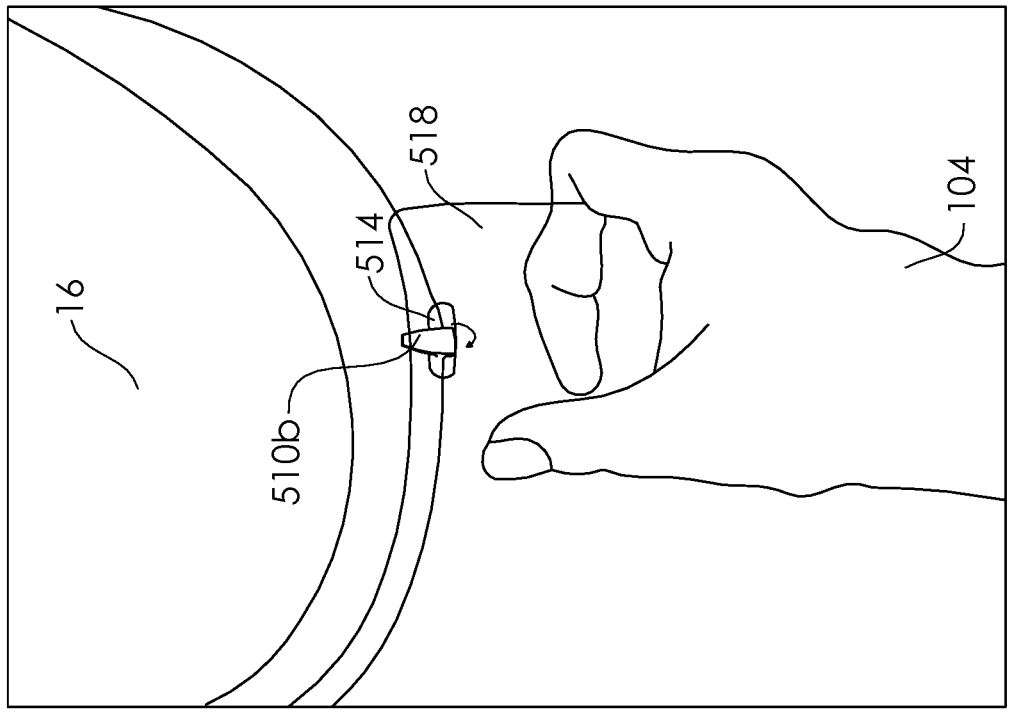
FIG. 22 is a perspective view of the facial shield being locked to the second side clip, according to an embodiment of the present disclosure.
Figure 21:
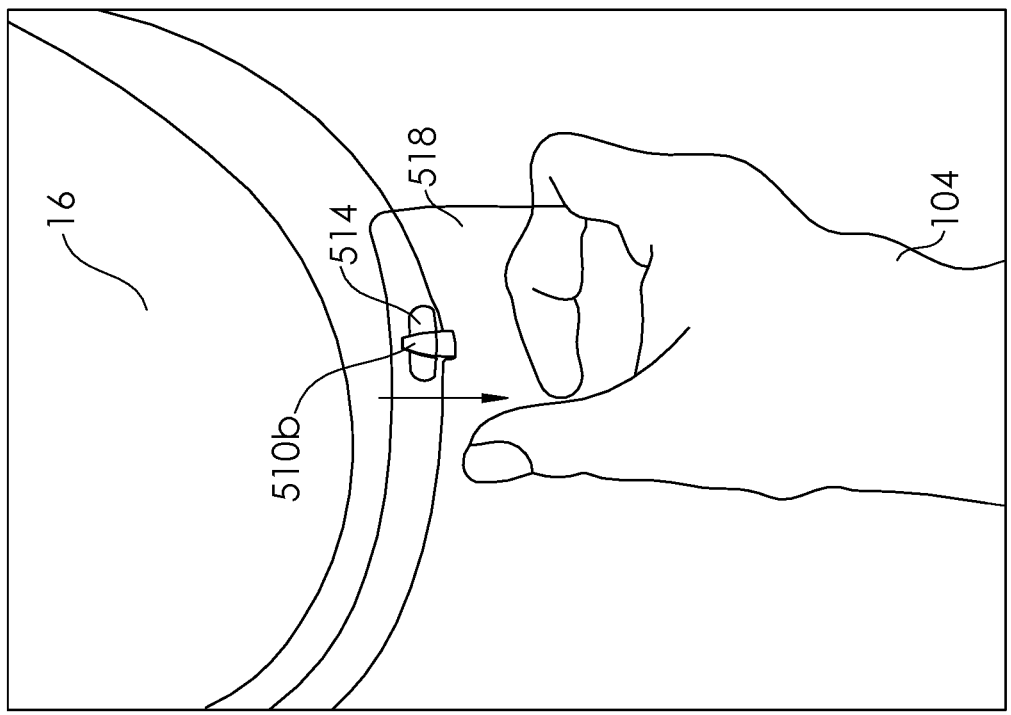
FIG. 21 is a perspective view of the facial shield being attached to the second side clip, according to an embodiment of the present disclosure.

In step 112, the assembler 104 wraps the opposite side of the facial shield 518 around the outer surface 522 of the head support 16 and places the hole 514 over the upper hook portion 540 of the side hook 510b, as shown in FIG. 20. As shown in detail in FIG. 12, the assembler 104 passes the hole 514 over the end 538 and onto the upper hook portion 540 of the hook portion 528 of the hook 510b. In step 114, the assembler 104 pulls the facial shield 518 downward (arrow, FIG. 21) to force a lower margin 517 of material surrounding the hole 514 over the bottom face 550 of a lower hook portion 542 of the hook portion 528, as shown in FIG. 13 and FIG. 22. An upper edge 544 of the hole 514 is forced against an upper ledge 546 of the base 526, and the right side of the facial shield 518 is forced further downward, slightly opening the gap $g_2$ (FIG. 6), such that a lower edge 548 of the hole 514 clears a bottom face 550 of a lower hook portion 542 of the hook portion 528. Turning to FIG. 14, when the hole 514 is released, and loses its slight deformation, the lower edge 548 of the hole 514 is snapped into its locked, rest position, above the bottom face 550, but below a lower ledge 552 of the base 526. The hole 514 is thus locked both in relation to the upper hook portion 540 and the lower hook portion 542. FIG. 23 illustrates the facial shield 518 fully assembled onto the head support 16. As shown in FIGS. 15-22, the facial shield 518 can be easily and securely attached to the head support 16 without touching the head support 16 at all.

FIG. 9 further illustrates a method 116 for removal of the facial shield 518 from the head support 16. In step 118, the user 104 unsnaps the hole 514 and removes the facial shield 518 from the side hook 510b. In step 120, the user 104 unsnaps the hole 516 and removes the facial shield 518 from the side hook 510a. In step 122, the user slides the facial shield 518 in relation to the head support 16 to unlock the hole 512 from the center hook 508, thus placing the facial shield 518 into the position of FIGS. 7, 10, and 15. In step 124, the user 104 completely removes the facial shield 518 from the head support 16. In step 126, the user 14 discards the facial shield 126. In some cases, the user 104 may also choose to discard the head support 16.

In other embodiments, any one or more of the holes 512, 514, 516 may be vertically elongated instead of horizontally elongated. One or more of the holes 512, 514, 516 may even be diagonally elongated. The facial shield 518 can be produced from standard sheet material and can be mass produced by a die cutting process thus significantly lowering the cost in comparison with traditional curved, single-shape facial shields. The locking and unlocking utilizing the hooks 508, 510 and the holes 512, 514, 516 provides quick yet secure assembly and quick removal and cleaning or disposal.

Figure 28:
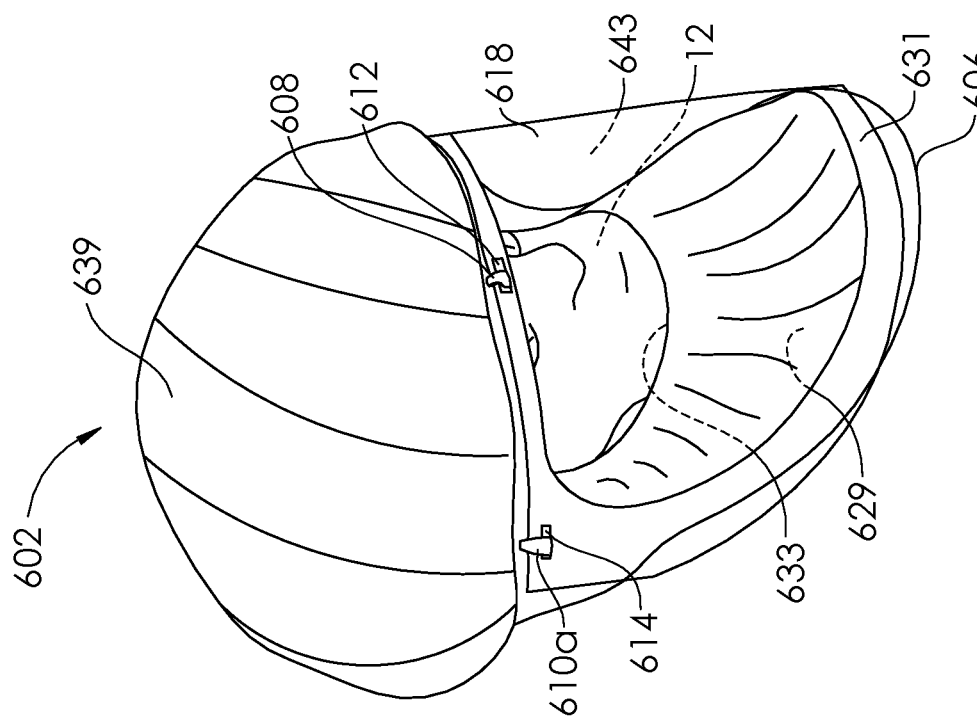
FIG. 28 is a perspective view of a personal protection system incorporating the facial shield and cuff of FIG. 27, according to an embodiment of the present disclosure.

A personal environmental protection system 602 is illustrated in FIGS. 24-27 and comprises a support portion 604 (e.g., head support) and a chin bar 606. The support portion 604 carries a center hook 608 and two side hooks 610a, 610b. The hooks 608, 610a, 610b are configured to engage holes 612, 614, 616 which extend through an upper extremity 627 of a facial shield 618, illustrated in FIG. 27. The facial shield 618 can comprise a clear sheet of the material previously described herein. The facial shield 618, however, further comprises a cuff 629, which may comprise a woven protective barrier. The cuff 629 is bonded to the facial shield by a seam 631 running substantially vertically along the right side 611, substantially horizontally along the lower extremity 625, and substantially vertically along the left side 613 of the facial shield 618. The cuff 629 includes an elastic inner perimeter 633 configured to fit snugly around a user's neck or lower head, to create a protected internal space 643 (FIG. 28). Turning to FIG. 25, the center hook 608 has a base 620 configured to couple to an outer surface 622 of the support portion 604, and a hook portion 624 having a maximum width $W_4$. The hook portion 624 may have a J-shape or an L-shape, or any other shape that may allow some level of hooking to occur. Each of the side hooks 610a, 610b have a base 626 configured to couple to the outer surface 622 of the support portion 604, and a hook portion 628 having a maximum width $W_5$. Each hole 614, 616 has a width $W_6$ that is greater than the maximum width $W_5$, and the hole 612 has a width $W_7$ that is greater than the maximum width $W_4$, thus allowing each hole 612, 614, 616 to fit completely over each hook 608, 610a, 610b. In some embodiments, the width $W_6$ may be configured to be at least 10% greater than the width $W_5$, or at least 25% greater than the width $W_5$. In some embodiments, the width $W_7$ may be configured to be at least 25% greater than the width $W_4$, or at least 50% greater than the width $W_4$, or at least 75% greater than the width $W_4$, or at least 100% greater than the width $W_4$. In some embodiments, the width $W_6$ may be configured to be between about 25% and about 100% greater than the width $W_5$. In some embodiments, the width $W_7$ may be configured to be between about 25% and about 100% greater than the width $W_4$. In some embodiments, the hole 616 has a first lateral edge 617 and a second lateral edge 619. Hole 614 may be described in the same manner. In some embodiments the first and second lateral edges 617, 619 can be simultaneously placed outside of the upper hook portion maximum width (width $W_5$) of an upper hook portion 640 of the side hook 610b (or side hook 610a) while the hole 612 remains engaged on the center hook 608, but only when the facial shield 618 is in a particular lateral position in relation to the center hook 608. This relation may be adjusted via sliding adjustment.

The hook portion 624 of the center hook 608 has a maximum thickness $t_3$, and the hook portion 628 of the side hooks 610 has a maximum thickness $t_4$. Hole 612 has a gap $g_3$ that is at least slightly greater than the maximum thickness $t_3$, thus allowing the hole 612 to fit completely over center hook 608. Holes 614, 616 each have a gap $g_4$ that is at least slightly greater than the maximum thickness $t_4$, thus allowing each hole 614, 616 to fit completely over each side hook 610a, 610b. Center hook 608 has an overhang 630, and a recess 632, between the overhang 630 and the base 626. To attach the facial shield 618 to the support portion 604, hole 612 is first inserted over the end 634 of the overhang 630 and the facial shield 618 is pulled down over the hook portion 624, toward the base 620 so that a border portion 636 of the facial shield 618, that is peripheral to hole 612, fits completely within the recess 632, with the facial shield 618 extending substantially vertically downward. The hole 612 is now locked over the base 620 of the center hook 608 in a somewhat similar manner, though not identical, to the way the second section 503 of the hole 512 is locked over the center hook 508 in FIG. 11. However, the locking is caused only by tension, with no sliding required. In some embodiments, a bottom portion 641 of the hole 612 can be configured to deform or flex, and snap over a bottom edge 649 of the center hook 608, similar to the snapping of the lower edge 548 over the bottom face 550 in FIGS. 13-14.

The facial shield 618 is then moved to the left so that the hole 612 slides to the far left on the hook portion 624 of the center hook 608. The hole 612 remains locked to the center hook 608 while being slid. Next, the hole 614 is inserted over the end 638 of an upper hook portion 640 of the hook portion 628 of the side hook 610a, and the right side 611 of the facial shield 618 is pulled down over the upper hook portion 640 toward the base 626. An upper edge 644 of the hole 614 is forced against an upper ledge 646 of the base 626, and the right side 611 of the facial shield 618 is forced further downward, slightly opening the gap $g_4$, such that a lower edge 648 of the hole 614 clears a bottom face 650 of a lower hook portion 642 of the hook portion 628 of the side hook 610a. When the hole 614 is released, and loses its slight deformation, the lower edge 648 of the hole 614 is snapped into its locked, rest position, above the bottom face 650, but below a lower ledge 652 of the base 626. The hole 614 is thus locked both in relation to the upper hook portion 640 and the lower hook portion 642. The facial shield 618 thus extends substantially vertically downward at its right side 611, as well as at its center. If needed, the facial shield 618 can now be moved slightly to the left, with the hole 614 sliding (in a locked position) along the side hook 610a and with the hole 612 sliding (in a locked position) along the center hook 608. The snapping process of the hole 614 and the side hook 610a can now be repeated with the hole 616 and the side hook 610b. The facial shield 618 is now securely in place on the support portion 604, with a few quick and simple snap and slide actions, as shown in FIG. 28. Removal of the facial shield 618 can be performed by substantially reversing the actions and steps. In other embodiments, any one or more of the holes 612, 614, 616 may be vertically elongated instead of horizontally elongated. One or more of the holes 612, 614, 616 may even be diagonally elongated.

Figure 29:
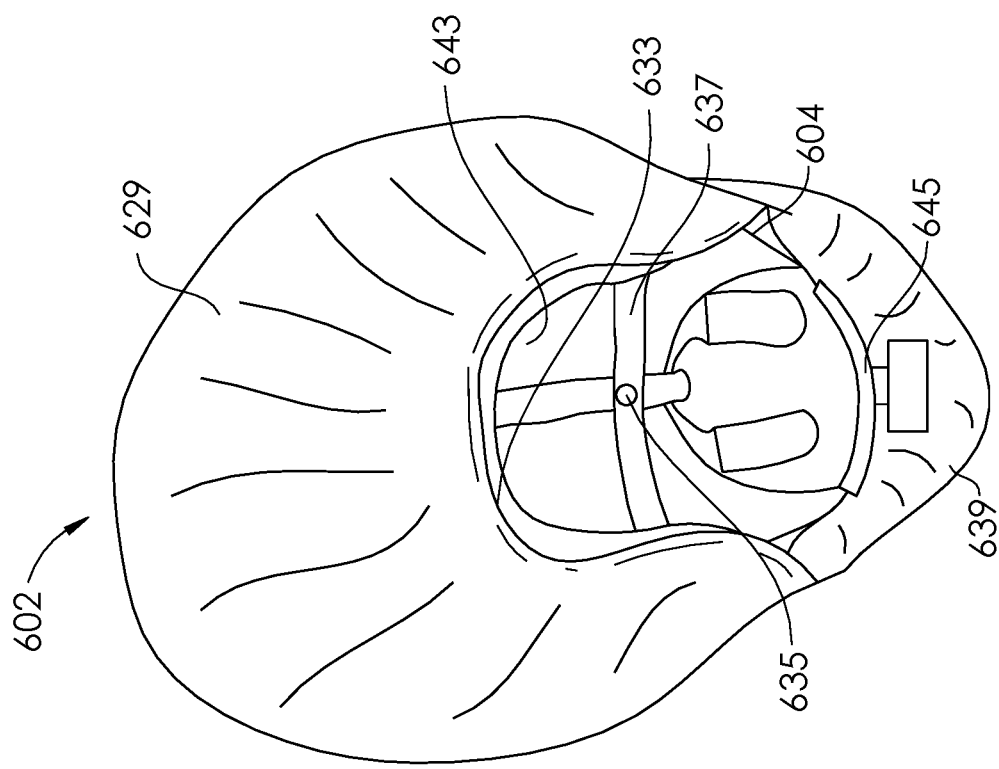
FIG. 29 is an underside view of the personal protection system of FIG. 28.

The personal protection system 240 is illustrated in its assembled configuration in FIGS. 28 and 29. The cuff 629 extends from the seam 631 and terminates in the elastic inner perimeter 633, forming an arc-shaped elastic window. An elastic band 637 is coupled to the cuff 629 (e.g., by sewing) and has a central snap 635 configured to secure the cuff 629 to the support portion 604 via a cooperative snap (adjacent, but not shown) held thereon. The elastic inner perimeter 633 is configured to fit snugly around a user's neck or lower head, to create the protected internal space 643. In some cases, the elastic inner perimeter 633 can be worn on the user's ears. In other cases, the elastic perimeter can be worn below the user's ears. In other cases, the elastic inner perimeter 633 can be pulled completely above or substantially above the user's ears. This particular positioning above the ears is useful, for example, if the user needs to use a stethoscope, which requires access to both ears and extends below the ears. The positioning may also be useful if the user is using one or more earphones (e.g., over ear or earbuds), so that an assistant may remove one of the earphones at a certain time in a procedure. Alternatively, if the user is using one earphone only, the user may choose to have the elastic inner perimeter 633 pulled above one ear and below the other ear. In some embodiments, a woven cloth covering 639 may be carried on and over the support portion 604. In other embodiments, the cuff 629 may be integral with the woven cloth covering 639, such that the window formed by the elastic inner perimeter 633 is first placed over the head of the user, and subsequently the woven cloth covering 639 is attached to the top of the support portion 604 (e.g., stretched over it), and the facial shield 618 is attached to the support portion 604, as described. An adjustable strap 645 may be used to create the appropriate fit around the user's head. The combination of the cuff 629 into the facial shield 618 allows disposability of portions of the personal environmental protection system 602 (facial shield 618, cuff 629, woven cloth covering 639) that may be more difficult to clean or maintain, while preserving reusability of the support portion 604, which may be more easily cleaned and reused. Any of the facial shields or cuffs described herein may be configured from biodegradable materials. Any of the materials described herein may be configured from reusable materials. In other embodiments, the cuff 629 may be incorporated with the facial shield 518 of FIG. 6. In alternative embodiments, any of the holes 512, 514, 516, 612, 614, 616 may be replaced by a hole, a notch, or a groove within a separate standoff or bracket that is attached to the facial shield 518, 618, or in a thickened portion of the facial shield 518, 618 that acts like a standoff or bracket. In other alternative embodiments, one or more of the hole/hook relationships may be replaced or augmented by a magnet/ferrous material relationship, or even a magnet/magnet relationship. For example, the facial shield 518, 618 carries one or more steel or 400 series stainless steel buttons or plates that is/are configured to releasably attached to one or more magnet carried by the outer surface 522, 622.

Figure 30:
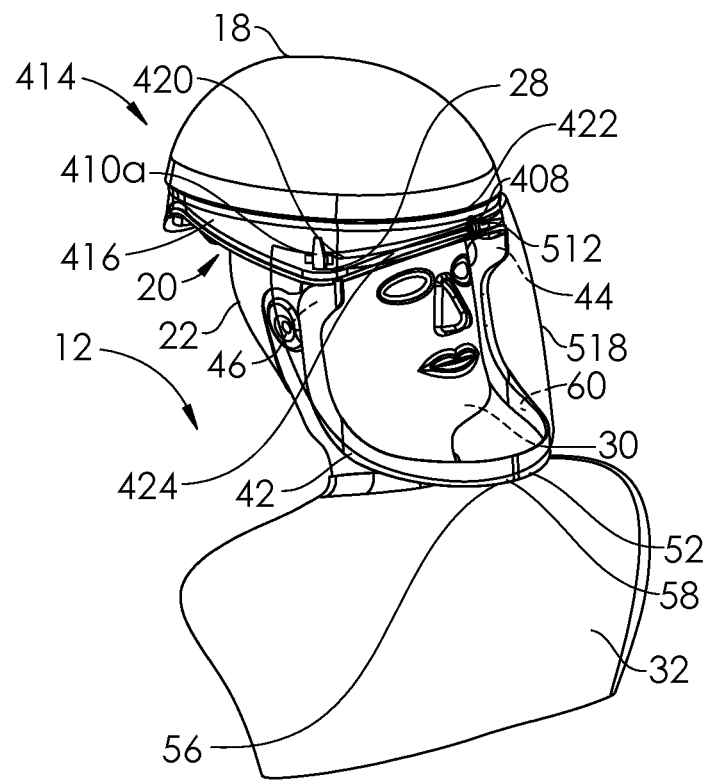
FIG. 30 is a perspective view of an alternative personal protection system in place on a user, according to an embodiment of the present disclosure.
Figure 31:
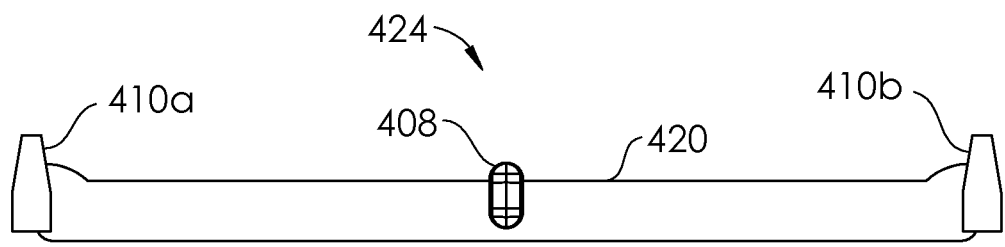
FIG. 31 is a hook strip assembly of the personal protection system of FIG. 30.

FIG. 30 illustrates a user 12 wearing a personal environmental protection system 414 that is similar to the personal environmental protection system 14 of FIG. 1. However, as illustrated in FIG. 31, a center hook 408 and two side hooks 410a, 410b are carried as a hook assembly 424. The center hook 408 and two side hooks 410a, 410b are carried are attached to a flexible strip 420. A back surface of the flexible strip 420 is attached to an outer surface 422 of a head support 416. By first constructing the hook assembly 424, a precision distance between each hook 408, 410a, 410b can be achieved. The manufacture of the head support 416 can also be simplified, because it does not have to have contours (slits and/or projections) to accommodate each hook 408, 410a, 410b. The flexible strip 420 may have an adhesive strip carried on its back surface. A user can remove a protective cover from the adhesive strip and then attached the flexible strip to the outer surface 422 of the head support 416 via the adhesive strip. The hook assembly can be centered and oriented on the head support 416 via a mark in the center of the head support 416 that corresponds to the location for the center hook 408. Because the head support 416 does not have to have the additional features to accommodate each hook, the head support 416 is more readily cleanable and, if appropriate, sterilizable. The hook assembly 424 can be disposable, or can be reusable, but may be configured for fewer reuses than the head support 416. In alternative embodiments, the backing of the flexible strip 420 may comprise a hooks and loops structure corresponding to a hooks and loop structure carried on the outer surface 422 of the head support 416.

While the foregoing is directed to embodiments of the present disclosure, other and further embodiments may be devised without departing from the basic scope thereof.

The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

For purposes of the present disclosure and appended claims, the conjunction "or" is to be construed inclusively (e.g., "an apple or an orange" would be interpreted as "an apple, or an orange, or both"; e.g., "an apple, an orange, or an avocado" would be interpreted as "an apple, or an orange, or an avocado, or any two, or all three"), unless: (i) it is explicitly stated otherwise, e.g., by use of "either . . . or," "only one of," or similar language; or (ii) two or more of the listed alternatives are mutually exclusive within the particular context, in which case "or" would encompass only those combinations involving non-mutually-exclusive alternatives. For purposes of the present disclosure and appended claims, the words "comprising," "including," "having," and variants thereof, wherever they appear, shall be construed as open-ended terminology, with the same meaning as if the phrase "at least" were appended after each instance thereof.

What is claimed is:

1. A protective headgear system comprising:
    a support configured to engage the head of a user;
    first, second, and third hooks carried on a perimeter of the support and horizontally spaced from each other;
    a facial shield comprising a polymeric sheet having an upper portion configured to be coupled to the support and a lower portion having a lower extremity, wherein the upper portion comprises a first hole, a second hole, and a third hole, each one of the first, second, and third holes horizontally spaced from the other two of the first, second, and third holes, wherein the first hole is between the second hole and the third hole;
    wherein the first hole is configured to be engaged with the first hook;
    wherein the second hole is configured to be engaged with the second hook;
    wherein the third hole is configured to be engaged with the third hook, wherein the first hook is located between the second hook and the third hook along the perimeter of the support;
    wherein the first hook comprises a hook portion having a maximum hook horizontal width, and wherein the first hole has a first hole horizontal width greater than the maximum hook horizontal width of the hook portion of the first hook; and
    wherein the facial shield has a first position in relation to the support such that the first hole can be placed in an unlocked manner around the hook portion of the first hook such that the second hole is not oriented for coupling to the second hook when the facial shield is overlayed in an extended condition over the perimeter of the support, and wherein the first hole is horizontally slidable on the first hook whereby the facial shield is placed into a second, locked position in relation to the support via the first hook and the first hole such that the second hole is oriented for coupling to the second hook when the facial shield is overlayed in an extended condition over perimeter of the support.

2. The system of claim 1, wherein when the facial shield is in the second position in relation to the support, the third hole can be placed in position for coupling to the third hook.

3. The system of claim 1, wherein the second hook comprises a base coupled to the support, an upper hook portion extending substantially vertically upward from the base, and a lower hook portion extending substantially vertically downward from the base.

4. The system of claim 3, wherein the third hook comprises a base coupled to the support, an upper hook portion extending substantially upward from the base, and a lower hook portion extending substantially downward from the base.

5. The system of claim 4, wherein the third hole is configured to be slid over the upper hook portion of the third hook and snapped over the lower hook portion of the third hook, thereby locking the facial shield to the third hook via the third hole.

6. The system of claim 3, wherein the second hole has a second hole vertical gap and a second hole horizontal width, and wherein the base of the second hook has a vertical thickness less than the second hole vertical gap, the base of the second hook further having a horizontal thickness less than the second hole horizontal width.

7. The system of claim 6, wherein the lower hook portion of the second hook has a vertical extension length from a lower portion of the base of the second hook, wherein the sum of (a) the vertical extension length of the lower hook portion of the second hook and (b) the vertical thickness of the base of the second hook is greater than (c) the second hole vertical gap.

8. The system of claim 3, wherein the second hole is configured to be slid over the upper hook portion of the second hook and snapped over the lower hook portion of the second hook, thereby locking the facial shield to the second hook via the second hole.

9. The system of claim 1, wherein the first hook comprises a base coupled to the support, an upper hook portion extending substantially upward from the base, and a lower hook portion extending substantially downward from the base.

10. The system of claim 9, wherein the first hook has a maximum vertical dimension and a vertical base thickness, and wherein the first hole has a first section having a first hole vertical gap and a second section horizontally adjacent the first section and having a second hole vertical gap, wherein the first hole vertical gap is greater than or equal to the maximum vertical dimension of the first hook, and wherein the second hole vertical gap is greater than the vertical base thickness and is less than the maximum vertical dimension.

11. The system of claim 1, wherein a distance along the perimeter between the second hook and the third hook is between about twelve inches and about fourteen inches.

12. The system of claim 1, wherein a distance between a horizontal center of the second hole and a horizonal center of the third hole is between twelve inches and fourteen inches.

13. The system of claim 1, further comprising a cuff coupled to the lower portion of the facial shield.

14. The system of claim 13, wherein the cuff comprises a first portion coupled to the lower portion of the facial shield and a second portion, opposite the first portion, the second portion configured to engage the neck of the user.

15. A facial shield configured to be coupled to a support configured to engage the head of a user and having first, second, and third hooks carried on a perimeter of the support and horizontally spaced from each other, wherein the first hook is located between the second hook and the third hook along the perimeter of the support, and wherein the first hook comprises an outwardly extending hook portion having a maximum vertical dimension and a base coupled to the support and having a vertical base thickness, the facial shield comprising:
  a polymeric sheet having an upper portion configured to be coupled to the support and a lower portion having a lower extremity, wherein the upper portion comprises a first hole, a second hole, and a third hole, each one of the first, second, and third holes horizontally spaced from the other two of the first, second, and third holes, wherein the first hole is between the second hole and the third hole; and
  the first hole comprising a first section having a first section vertical gap and a second section horizontally adjacent the first section and having a second section vertical gap, wherein the second section vertical gap is between 0.225 inch and 0.68 inch, and wherein the first section vertical gap is greater than the second section vertical gap, wherein the first section vertical gap of the first hole is greater than or equal to the maximum vertical dimension of the first hook, and wherein the second section vertical gap of the first hole is greater than the vertical base thickness of the base of the first hook and is less than the maximum vertical dimension of the first hook, and wherein the first hole is horizontally slidable in relation to the first hook such that the facial shield is thereby locked to the first hook via the first hole.

16. The facial shield of claim 15, wherein the second section vertical gap is between 0.30 inch and 0.45 inch.

17. The facial shield of claim 15, wherein the first section vertical gap is greater than 0.68 inch.

18. The facial shield of claim 15, wherein the second hole has a vertical gap and a horizontal width, the horizontal width greater than the vertical gap.

19. The facial shield of claim 18, wherein the third hole has a vertical gap and a horizontal width, the horizontal width greater than the vertical gap.

20. The facial shield of claim 15, further comprising a cuff coupled to the lower portion of the polymeric sheet.

21. The facial shield of claim 20, wherein the cuff comprises a first portion coupled to the lower portion of the polymeric sheet and a second portion, opposite the first portion, the second portion configured to engage the neck of the user.

22. The facial shield of claim 15, wherein the second hole is snappably engageable with the second hook.

23. The facial shield of claim 22, wherein the third hole is snappably engageable with the third hook.

24. The facial shield of claim 15, wherein the facial shield has a first position in relation to the support such that the first hole can be placed in an unlocked manner around the hook portion of the first hook and the second hole is not oriented to be coupled to the second hook, and wherein, when the first hole is horizontally slid in relation to the first hook such that the facial shield is locked to the first hook via the first hole, the facial shield is placed into a second position in relation to the support wherein the second hole is oriented for coupling to the second hook.

25. The facial shield of claim 15, wherein the polymeric sheet has a thickness of between 0.010 inch and 0.020 inch.

26. The facial shield of claim 15, wherein the facial shield is configured to be coupled to the support without requiring the user or a person aiding the user to touch the support.

27. The facial shield of claim 15, wherein the facial shield is configured to be coupled to the support without requiring the user or a person aiding the user to contact the support with a glove or a hand.

* * * * *